United States Patent
Kanbara et al.

(10) Patent No.: US 9,372,136 B2
(45) Date of Patent: Jun. 21, 2016

(54) AGENT FOR IMPROVING CANCER CELL ADHESIVENESS

(75) Inventors: Hisashige Kanbara, Oyama (JP); Masaru Tanaka, Yonezawa (JP); Satomi Yagi, Yonezawa (JP); Takashi Hoshiba, Yonezawa (JP); Mayo Nikaidou, Yonezawa (JP); Kazuhiro Satou, Yonezawa (JP); Chikako Satou, Yonezawa (JP)

(73) Assignee: HITACHI CHEMICAL COMPANY, LTD., Tokyo (JP)

( * ) Notice: Subject to any disclaimer, the term of this patent is extended or adjusted under 35 U.S.C. 154(b) by 133 days.

(21) Appl. No.: 14/126,049

(22) PCT Filed: Jun. 11, 2012

(86) PCT No.: PCT/JP2012/064932
§ 371 (c)(1),
(2), (4) Date: Feb. 11, 2014

(87) PCT Pub. No.: WO2012/173097
PCT Pub. Date: Dec. 20, 2012

(65) Prior Publication Data
US 2014/0178890 A1 Jun. 26, 2014

(30) Foreign Application Priority Data

Jun. 13, 2011 (JP) .................................. 2011-131241
May 30, 2012 (JP) .................................. 2012-123228

(51) Int. Cl.
*G01N 1/40* (2006.01)

(52) U.S. Cl.
CPC ...................... *G01N 1/405* (2013.01)

(58) Field of Classification Search
None
See application file for complete search history.

(56) References Cited

U.S. PATENT DOCUMENTS

| 7,781,551 B2 | 8/2010 | Pacetti et al. |
| 2001/0019029 A1 | 9/2001 | Tai et al. |

FOREIGN PATENT DOCUMENTS

| CN | 1922304 A | 2/2007 |
| CN | 101583722 A | 11/2009 |

(Continued)

OTHER PUBLICATIONS

Yagi et al., Selective Adhesion of Human Cancer Cells on Blood Compatible Polymer, Polymer Preprints, Regenerative Medicine, vol. 60, No. 1, Disk 1, May 10, 2011.*

(Continued)

*Primary Examiner* — Vu A Nguyen
(74) *Attorney, Agent, or Firm* — Fitch Even Tabin & Flannery LLP

(57) ABSTRACT

A polymer comprising a constitutional unit represented by the following formula (1) is useful because when the polymer is applied to a surface of a cancer cell enrichment filter, adhesiveness of cancer cells to the filter surface can be improved so that an enrichment ratio of the cancer cells can be improved. In the formula (1), $R^1$ is a hydrogen atom or a methyl group, $R^2$ is a methyl group or an ethyl group and m is 1 to 3.

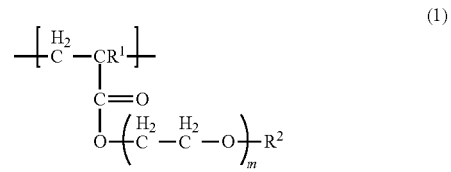

(1)

16 Claims, 6 Drawing Sheets

(56) References Cited

FOREIGN PATENT DOCUMENTS

| CN | 101769930 A | 7/2010 | | |
|---|---|---|---|---|
| WO | WO 00/02599 | 1/2000 | | |
| WO | WO 2004/087228 A1 | 10/2004 | | |
| WO | WO 2004087228 A1 * | 10/2004 | .............. | A61L 15/24 |
| WO | 2006/116327 A1 | 11/2006 | | |

OTHER PUBLICATIONS

Hosokawa et al., Size-Selective Microcavity Array for Rapid and Efficient Detection of Circulating Tumor Cells, Anal. Chem. 2010, 82, 6629-6635.*

Derwent Account No. 2004-757713.*

Office Action of CN Appln. No. 201280029309.2 dated Aug. 19, 2014.

Dietrich et al., Au Nanoparticles Stabilised by PEGylated low Generation PAMAM Dendrimers: Design, Characterisation and Properties, Journal of Colloid and Interface Science, vol. 359, No. 2, Mar. 24, 2011, XP028209409, p. 454-460.

Lo et al., Mixed Micelle Systems formed from Critical Micelle Concentration and temperature-Sensitive Diblock Copolymers for Doxorubicin Delivery, Biomaterials, vol. 30, Nos. 23-24, Aug. 1, 2009, XP026149161 p. 3961-3970.

Hoshiba et al., Regulation of Cancer cell Adhesion on Biocompatible Polymer-Coated Surfaces, Journal of Nanomedicine & Nanotechnology, vol. 1, No. S1, Jan. 1, 2012, XP055158615.

Hoshiba et al., Cancer Cell Attachment on a Blood Compatible Polymer, poly(2-methoxyethyl acrylate) (PMEA), retrieved from Internet: URL:http://abstracts.biomaterials.org./data/papers/2014/0332000409.pdf, Mar. 26, 2014, XP055158629.

EP Search Report of Appln. No. 12801028.7 dated Jan. 8, 2015 in English.

Vona et al., Enrichment, Immunomorphological, and Genetic characterization of Fetal Cells Circulating in Material Blood, American Journal of Pathology, vol. 160, No. 1, Jan. 2002, pp. 51-58.

Kahn et al., Enumeration of Circulating Tumor Cells in the Blood of Breast Cancer Patients After Filtration Enrichment: Correlation with Disease Stage, Breast Cancer Research and Treatment, 86, 2004, pp. 237-247.

Yuen et al., Microchip Module for Blood Sample Preparation and Nucleic Acid Amplification Reactions, Genome Research, 11, pp. 405-412, 2001.

Mohamed et al., Development of a Rare cell Fractionation Device: Application for Cancer Detection, IEEE Trans Nanobioscience, vol. 3, No. 4, Dec. 2004, pp. 251-256.

International Search Report of Int'l App. No. PCT/JP2012/064932 dated Sep. 25, 2012 in English.

Yagi et al., Selective Adhesion of Human Cancer Cells on Blood Compatible Polymer, Polymer Preprints, Regenerative Medicine, vol. 60, No. 1, Disk 1, May 10, 2011, with partial English translation.

Yagi et al., Manufacture of Polymer Surface with Both Non-Adhesive Property of Blood cells and Adhesive Property of Cancer Cells, Regenerative Medicine, vol. 10, Special Extra Issue, Feb. 1, 2011, p. 264 with partial English translation.

Hosokawa et al., Development of Microfluidic Device for Rapid Detection of Circulating Tumor Cells, Chemical Sensors, vol. 26, Supplement B, Sep. 2, 2010, pp. 40-42.

Hosokawa et al., Development of Microdevice for Highly Efficient Detection of Circulating Tumor Cell from Whole Blood, The Chemical Society of Japan Koen Yokoshu, Vo. $90^{th}$, No. 3, Mar. 12, 2010, p. 659.

Zheng et al., 3D Microfilter Device for Viable Circulating Tumor Cell (CTC) Enrichment from Blood, Biomed Microdevices, vol. 13, No. 1, Feb. 2011, pp. 203-213.

Hoshiba et al. Analysis of the Mechanism of Cancer Cell Adhesion of Blood Compatible Polymer, Polymer Preprints, vol. 61, No. 1, May 15, 2012 with partial English translation.

Yagi et al., Selective Adhesion of Human Cancer Cells on poly(2-methoxyethyl acrylate) (Poly(2-methoxyethylacrylate) The Annual Meeting of the Japanese Society for Biomaterials Yokoshu, vol. 33, Nov. 21, 2011, p. 306 with partial English translation.

International Prel. Report on Patentability of International Appl. PCT/JP2012/064932 dated Jan. 3, 2014 in English.

Office Action of Chinese Appln. No. 201280029309.2 dated Oct. 20, 2015.

* cited by examiner

AGENT FOR IMPROVING CANCER CELL ADHESIVENESS

TECHNICAL FIELD

The present invention relates to an agent for improving cancer cell adhesiveness. More particularly, it relates to an agent for improving cancer cell adhesiveness, a cancer cell enrichment filter and a method for testing cancer cells.

BACKGROUND ART

Enrichment of cancer cells is extremely significant in research and clinical aspects, and if cancer cells present in blood can be enriched, the enriched cancer cells can be applied to the diagnosis of cancer. For example, the most significant factor of a prognosis and a treatment of cancer is whether or not cancer cells have metastasized at the time of first medical examination or treatment. If cancer cells are spread to peripheral blood at an early stage, it is a useful method for determining disease progression of the cancer to detect circulating tumor cells (hereinafter sometimes referred to as the "CTCs").

In a general cancer patient who has just started suffering from a metastasis, however, merely one CTC is present in his/her blood per ten billion blood cells. On the contrary, there are an overwhelmingly large number of blood components such as erythrocytes and leucocytes in blood. Accordingly, it is extremely difficult to enrich CTCs in a very low concentration so as to highly sensitively, highly efficiently and highly specifically analyze the CTCs. If the CTCs are enriched by a method using, for example, magnetic beads, density gradient centrifugation, a microchannel or a flow cytometer, it is necessary to perform a complicated treatment as well as the recovery rate is poor in some cases.

As another technique to segregate/enrich CTCs, a method using a polycarbonate filter has been proposed (see, for example, Non Patent Literatures 1 and 2). Furthermore, a technique to segregate/enrich CTCs by utilizing a difference in size has also been proposed (see, for example, Non Patent Literatures 3 to 5 and Patent Literature 1).

It is known that contact of blood with a surface of a medical material for an artificial heart-lung machine or the like causes an adverse reaction such as induction of thrombus formation or hemolysis due to activation of a complement system or activation of blood platelets. It has been reported that it is effective, for solving this problem, to coat a surface of a medical material with a prescribed compound (see, for example, Patent Literature 2).

CITATION LIST

Patent Literature

Patent Literature 1: US Patent Application Publication No. 2001/0019029
Patent Literature 2: International Publication No. WO2004/087228

Non Patent Literature

Non Patent Literature 1: Vona G, et al., "Enrichment, immunomorphological, and genetic characterization of fetal cells circulating in material blood", Am J. Pathol. 160(1): 51-8 (2002)
Non Patent Literature 2: Kahn H J, et al., "Enumeration of circulating tumor cells in the blood of breast cancer patients after filtration enrichment: correlation with disease stage", Breast Cancer ResTreat; 86(3): 237-47 (2004)
Non Patent Literature 3: Wilding P, et al., "Integrated Cell Isolation and Polymerase Chain Reaction Analysis Using Silicon Microfilter Chambers", Anal Biochem. 257(2): 95-100 (1998)
Non Patent Literature 4: Yuen P K, et al., "Microchip module for blood sample preparation and nucleic acid amplification reactions", Genome Res. 11(3): 405-12 (2001)
Non Patent Literature 5: Mohamed H, et al., "Development of a rare cell fractionation device: application for cancer detection.", IEEE Trans Nanobioscience 3(4): 251-6 (2004)

SUMMARY OF INVENTION

Technical Problem

Cancer cells such as CTCs have a larger size than blood cells present in blood, such as erythrocytes, leucocytes and blood platelets. Therefore, theoretically, cancer cells can be enriched by removing these blood cell components by applying mechanical filtration.

A membrane filter described in each of Non Patent Literatures 1 and 2 has, however, randomly distributed pores and the pore size is ununiform, and therefore, a recovery rate of cancer cells is poor in some cases. Furthermore, even in using a filter, as described in each of Non Patent Literatures 3 to 5 and Patent Literature 1, having a pore size and a thickness accurately controlled, it is sometimes difficult to enrich cancer cells with accuracy sufficiently high for precise analysis.

The present invention was achieved in consideration of the aforementioned problems, and an object of the present invention is to provide an agent for improving cancer cell adhesiveness that is capable of improving adhesiveness of cancer cells. Another object of the present invention is to provide a cancer cell enrichment filter whose surface is coated with the agent for improving cancer cell adhesiveness. Still another object of the present invention is to provide a method for testing cancer cells comprising a step of filtering peripheral blood with the cancer cell enrichment filter.

Solution to Problem

There has been a conventional problem in which contact of blood with a surface of a medical material for an artificial heart-lung machine or the like causes an adverse reaction such as induction of thrombus formation or hemolysis due to activation of a complement system or activation of blood platelets. It is known that even if blood comes into contact with a surface of a medical material, adhesiveness of blood cell components to the surface of the medical material can be lowered by coating the surface of the medical material with a polymer comprising a constitutional unit represented by the following formula (1), so that the adverse reaction such as the induction of thrombus formation or hemolysis can be inhibited. Such a property to inhibit the thrombus formation or hemolysis is designated as blood compatibility.

The present inventors have first found that a material surface coated with the polymer comprising the constitutional unit represented by the following formula (1) unexpectedly shows improved adhesiveness to cancer cells while showing lowered adhesiveness to blood cell components, and thus, the present invention was accomplished.

Specifically, the present invention provides an agent for improving cancer cell adhesiveness consisting of a polymer comprising a constitutional unit represented by the following formula (1):

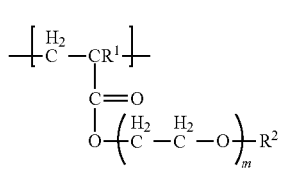

(1)

In the formula (1), $R^1$ is a hydrogen atom or a methyl group, $R^2$ is a methyl group or an ethyl group, and m is 1 to 3.

When the agent for improving cancer cell adhesiveness of the present invention is applied to a surface of a cancer cell enrichment filter, the adhesiveness of cancer cells to the surface of the filter can be improved, so as to improve an enrichment ratio of cancer cells.

When the surface of a cancer cell enrichment filter is subjected to a surface treatment for improving cell adhesiveness in order to improve the enrichment ratio of cancer cells, not only the adhesiveness of cancer cells such as CTCs but also the adhesiveness of the blood cell components is improved in general. Therefore, the enrichment ratio of cancer cells is not improved as a result, and hence desired enrichment performance cannot be attained. On the contrary, the agent for improving cancer cell adhesiveness of the present invention can simultaneously satisfy characteristics in a trade-off relationship, that is, non-adhesiveness of blood cell components and adhesiveness of cancer cells.

Furthermore, the present invention provides a method for improving adhesiveness of cancer cells to a substrate comprising a step of coating the substrate with a polymer comprising a constitutional unit represented by the following formula (1):

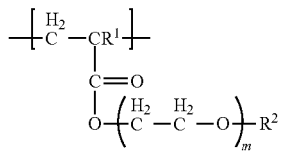

(1)

In the formula (1), $R^1$ is a hydrogen atom or a methyl group, $R^2$ is a methyl group or an ethyl group, and m is 1 to 3.

The present invention further provides use of a polymer comprising a constitutional unit represented by the following formula (1) for improving cancer cell adhesiveness:

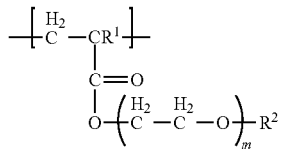

(1)

In the formula (1), $R^1$ is a hydrogen atom or a methyl group, $R^2$ is a methyl group or an ethyl group, and m is 1 to 3.

The present invention further provides application of a polymer comprising a constitutional unit represented by the following formula (1) to improvement of cancer cell adhesiveness:

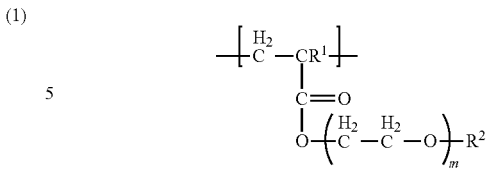

In the formula (1), $R^1$ is a hydrogen atom or a methyl group, $R^2$ is a methyl group or an ethyl group, and m is 1 to 3.

The present invention further provides application of a polymer comprising a constitutional unit represented by the following formula (1) to production of an agent for improving cancer cell adhesiveness:

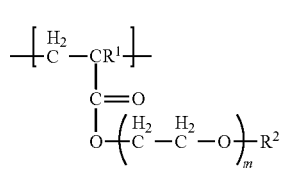

(1)

In the formula (1), $R^1$ is a hydrogen atom or a methyl group, $R^2$ is a methyl group or an ethyl group, and m is 1 to 3.

The present invention further provides a cancer cell enrichment filter consisting of a substrate having a plurality of through holes, wherein at least a part of the substrate is coated with a polymer comprising a constitutional unit represented by the following formula (1):

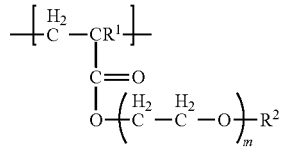

(1)

In the formula (1), $R^1$ is a hydrogen atom or a methyl group, $R^2$ is a methyl group or an ethyl group, and m is 1 to 3.

The polymer may consist of a constitutional unit represented by the above formula (1). Furthermore, it is preferable that $R^1$ is a hydrogen atom, $R^2$ is a methyl group, and m is 1. Alternatively, $R^1$ may be a hydrogen atom, $R^2$ may be an ethyl group, and m may be 2, or $R^1$ may be a methyl group, $R^2$ may be a methyl group, and m may be 2. Besides, the polymer preferably has a number average molecular weight of 10,000 to 300,000.

Such a polymer can further improve the cancer cell adhesiveness.

The present invention further provides a cancer cell enrichment filter consisting of a substrate which has a plurality of through holes and at least a part of which is coated with the above polymer.

According to the cancer cell enrichment filter of the present invention, cancer cells present in a blood sample can be enriched to a high enrichment ratio.

The through holes preferably have an average pore size of 5 μm or more and less than 30 μm and an average aperture ratio of 5% or more and less than 50%, and are preferably formed by an electrocasting method. The substrate is preferably made of a metal. The metal is preferably selected from the group consisting of copper, nickel, a copper-nickel alloy, and any of these metals and alloy having a gold-plated surface.

According to this cancer cell enrichment filter, cancer cells present in a blood sample can be enriched to a further higher enrichment ratio.

The present invention further provides a method for detecting presence of cancer cells comprising a filtration step of filtering peripheral blood with the cancer cell enrichment filter.

According to the method of the present invention, the presence of cancer cells such as CTCs in peripheral blood collected from a patient can be easily detected.

The test method may further include a step of analyzing a gene of cells having been enriched in the filtration step, and may further include a step of culturing cells having been enriched in the filtration step.

Since the cells are merely slightly damaged in the filtration step, the step of analyzing a gene of the enriched cells or the step of culturing the cells can be performed. When the method for detecting presence of cancer cells of the present invention further includes such a step, the presence of cancer cells such as CTCs in peripheral blood can be more accurately detected.

Advantageous Effects of Invention

The present invention provides an agent for improving cancer cell adhesiveness, a cancer cell enrichment filter whose surface is coated with the agent for improving cancer cell adhesiveness and a method for testing cancer cells comprising a step of filtering peripheral blood with the cancer cell enrichment filter.

DESCRIPTION OF EMBODIMENTS

Figure 1:
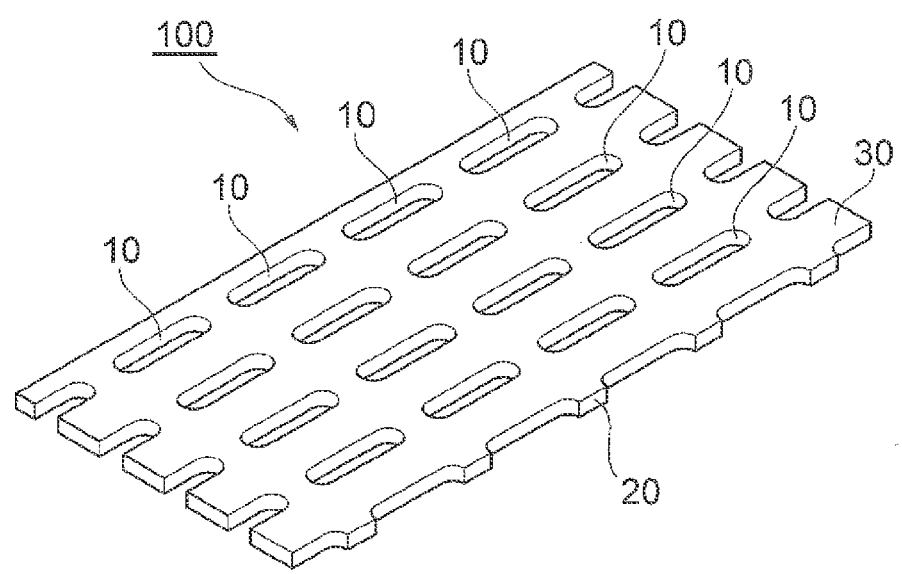
FIG. 1 is a schematic diagram illustrating an embodiment of a cancer cell enrichment filter.

Preferred embodiments of the present invention will now be described with reference to accompanying drawings if necessary. It is noted that a like reference numeral is used to refer to a like element shown in a drawing, so as to avoid redundancy. Besides, a part of the drawing is exaggerated to be easily understood, and a size ratio in the drawing does not necessarily accord with that mentioned in the description.

In one embodiment, an agent for improving cancer cell adhesiveness consists of a polymer comprising a constitutional unit represented by the following formula (1):

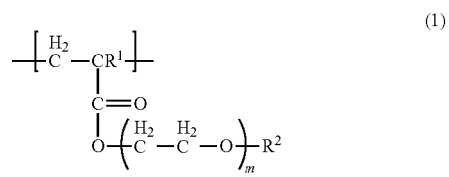

In the above formula (1), $R^1$ is a hydrogen atom or a methyl group, $R^2$ is a methyl group or an ethyl group, and m is 1 to 3. A number average molecular weight of the polymer is preferably 10,000 to 300,000. If the number average molecular weight is 10,000 or less, the polymer is in the form of a liquid and hence is difficult to handle in some cases. Furthermore, in some cases, the polymer is difficult to attain a number average molecular weight of 300,000 or more by general radical polymerization.

The polymer can be typically produced by polymerization, performed by a general method, of a solution of a monomer represented by the following formula (2) with an appropriate initiator added. A temperature at which the polymerization is performed is preferably 40° C. to 100° C., more preferably 60° C. to 90° C., and further more preferably 70° C. to 80° C. A pressure at which the polymerization is performed is preferably normal pressure.

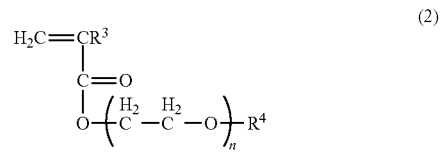

In the above formula (2), $R^3$ is a hydrogen atom or a methyl group, $R^4$ is a methyl group or an ethyl group, and n is 1 to 3.

In the polymerization, a solvent capable of dissolving the monomer represented by the above formula (2) can be used as a solvent. Examples of the solvent include aliphatic or aromatic organic solvents, and more specifically, examples include ether solvents such as dioxane, tetrahydrofuran and diethyl ether; halogenated aromatic hydrocarbons such as o-dichlorobenzene; amides such as N,N-dimethylformamide; sulfoxides such as dimethyl sulfoxide; aromatic hydrocarbons such as benzene and toluene; and aliphatic hydrocarbons such as hexane and pentane, among which an ether solvent such as dioxane is preferably used.

In one embodiment, an agent for improving cancer cell adhesiveness, consists of a polymer consisting of a constitutional unit represented by the above formula (1).

In the agent for improving cancer cell adhesiveness, a combination of $R^1$, $R^2$ and m of the above formula (1) is preferably any one of the following combinations (a) to (h):

(a) $R^1$ is a hydrogen atom, $R^2$ is a methyl group, and m is 1 to 2;
(b) $R^1$ is a hydrogen atom, $R^2$ is a methyl group, and m is 3;
(c) $R^1$ is a hydrogen atom, $R^2$ is an ethyl group, and m is 1 to 2;
(d) $R^1$ is a hydrogen atom, $R^2$ is an ethyl group, and m is 3;
(e) $R^1$ is a methyl group, $R^2$ is a methyl group, and m is 1 to 2;
(f) $R^1$ is a methyl group, $R^2$ is a methyl group, and m is 3;
(g) $R^1$ is a methyl group, $R^2$ is an ethyl group, and m is 1 to 2; and
(h) $R^1$ is a methyl group, $R^2$ is an ethyl group, and m is 3.

When the combination of $R^1$, $R^2$ and m is any one of the above combinations, it is possible to further improve an effect of lowering adhesiveness of blood cell components as well as improving adhesiveness of cancer cells to a substrate coated with the agent for improving cancer cell adhesiveness.

In one embodiment, an agent for improving cancer cell adhesiveness is a random copolymer, a block copolymer or a graft copolymer of a monomer represented by the above formula (2) and another polymerizable monomer.

Examples of the monomer polymerizable with the monomer represented by the above formula (2) include: alkylacrylamides such as acrylamide, t-butyl acrylamide, n-butyl acrylamide, i-butyl acrylamide, hexyl acrylamide and heptyl acrylamide; N,N-dialkylacrylamides such as N,N-dimethylacrylamide and N,N-diethylacrylamide; amino alkyl acrylates such as amino methyl acrylate, amino ethyl acrylate and amino isopropyl acrylate; diamino alkyl acrylate such as diamino methyl acrylate, diamino ethyl acrylate and diamino butyl acrylate; N,N-dialkyl methacrylamides such as methacrylamide, N,N-dimethylmethacrylamide and N,N-diethylmethacrylamide; amino alkyl methacrylates such as amino methyl methacrylate and amino ethyl methacrylate; diamino alkyl methacrylates such as diamino methyl methacrylate and diamino ethyl methacrylate; alkyl acrylates such as methyl acrylate, ethyl acrylate, isopropyl acrylate, butyl acrylate, hexyl acrylate and 2-ethylhexyl acrylate; alkyl methacrylates such as methyl methacrylate, ethyl methacrylate, butyl methacrylate and hexyl methacrylate; alkoxy(meth)acrylates such as methoxy(meth)acrylate; alkoxy alkyl(meth)acrylate such as methoxy ethyl(meth)acrylate; and glycidyl methacrylate and propylene.

The monomer to be polymerized with the monomer represented by the above formula (2) may be one or more monomers selected from the group consisting of alkyl acrylate, alkyl methacrylate, alkoxy(meth)acrylate, alkoxy alkyl (meth)acrylate, glycidyl methacrylate and propylene.

The copolymer of the monomer represented by the above formula (2) and the above-described polymerizable monomer can be any one of a random copolymer, a block copolymer and a graft copolymer, and may be produced by any of random polymerization, ion polymerization, polymerization utilizing a macromer and the like.

When the monomer represented by the above formula (2) and the polymerizable monomer are copolymerized with each other, the content of the monomer represented by the above formula (2) is preferably 30 to 99% by mass and more preferably 50 to 99% by mass in the resulting copolymer.

The polymer comprising the constitutional unit represented by the above formula (1) can be typically produced by polymerization performed by random polymerization, ion polymerization, photopolymerization, polymerization utilizing a macromer or the like with an initiator appropriate for the solution of the monomer represented by the above formula (2) added thereto, and as occasion demands, with one or more of the polymerizable monomers added thereto. A temperature at which the polymerization is performed is preferably 40° C. to 100° C., more preferably 60° C. to 90° C. and further more preferably 70° C. to 80° C. A pressure at which the polymerization is performed is preferably normal pressure.

In the polymerization, a solvent capable of dissolving the monomer represented by the above formula (2) and the polymerizable monomer can be used as a solvent. Examples of the solvent include aliphatic or aromatic organic solvents, and more specifically, examples include ether solvents such as dioxane, tetrahydrofuran and diethyl ether; halogenated aromatic hydrocarbons such as o-dichlorobenzene; amides such as N,N-dimethylformamide; sulfoxides such as dimethyl sulfoxide; aromatic hydrocarbons such as benzene and toluene; and aliphatic hydrocarbons such as hexane and pentane, among which an ether solvent such as dioxane is preferably used.

When the agent for improving cancer cell adhesiveness is applied to a surface of a substrate of a cancer cell enrichment filter or the like, blood compatibility is imparted, and hence, if the filter is brought into contact with blood, activation of blood components can be inhibited, so as to reduce adhesion of blood cell components to the filter. Furthermore, since the cancer cell enrichment filter to which the agent for improving cancer cell adhesiveness is applied is good in adhesiveness to various cancer cells, cancer cells can be efficiently enriched.

Although the polymer comprising the constitutional unit represented by the above formula (1) has, in its molecule, an ether bond and an ester bond as a polar group, such a polar group does not show strong electrostatic interaction with a biological component differently from a nitrogen atom (an amino group or an imino group), a carboxyl group and the like. Furthermore, since the polymer has no large hydrophobic group, the hydrophobic interaction is also small. It is therefore presumed that the polymer comprising the constitutional unit represented by the above formula (1) has low activity against blood and shows excellent blood compatibility.

In contact between a medical material surface and protein present in a biological tissue or blood, it is preferable that adsorption/denaturation or activation of the protein does not occur, and for this purpose, it is regarded useful to reduce the hydrophobic interaction and the electrostatic interaction, that is, large interaction working between substances. Also from this point of view, the surface to which the agent for improving cancer cell adhesiveness is applied can be provided with a suitable surface structure.

Furthermore, since the surface to which the agent for improving cancer cell adhesiveness is applied has moderate hydrophilicity, even when it comes into contact with blood, blood platelets are merely slightly adhered thereto, and thus, excellent blood compatibility is shown. Moreover, it is presumed that interaction with a biological component via a hydrogen bond derived from a hydroxyl group, denaturation of adsorbed protein and the like can be inhibited.

By applying the agent for improving cancer cell adhesiveness to the surface of the substrate of the cancer cell enrichment filter or the like, adhesion to the filter of blood cell components such as erythrocytes, leucocytes and blood platelets can be reduced, and at the same time, cancer cells can be selectively and efficiently captured. The details of the mechanism of showing this function has not been clarified yet, but the present inventors presume that the mechanism can be explained by using concept of intermediate water.

Specifically, it seems that water in contact with the substrate to which the agent for improving cancer cell adhesiveness is applied includes (1) free water that has weak interaction with the agent for improving cancer cell adhesiveness and is molten at 0° C.; (2) unfreezable water that has strong interaction with the agent for improving cancer cell adhesiveness and does not freeze even at −100° C.; and (3) intermediate water that has interaction intermediate between the free water and the unfreezable water and freezes at a temperature lower than 0° C. Normal blood cells form a hydration shell with the unfreezable water, the intermediate water, the free water and the like in contact with the agent for improving cancer cell adhesiveness, and hence are stabilized owing to this hydration structure, but the unfreezable water strongly affected by the structure of the agent for improving cancer cell adhesiveness is probably camouflaged by the intermediate water, so that adhesion of the normal blood cells to the substrate surface is inhibited. On the other hand, since cancer cells are different from the normal cells in expression of sugar chains on cell surfaces, the hydration structure is probably disordered as compared with that in the normal blood cells. This seems to disturb the structure of the intermediate water on the substrate surface, so that the adhesiveness of the cancer cells to the substrate surface can be improved.

The agent for improving cancer cell adhesiveness is applicable to all the types of cancer cells, and is preferably applied to epithelial cell-derived cancers that easily infiltrate into blood vessels, and among such cancers, the agent is particularly preferably applied to lung cancers, digestive cancers such as colorectal cancers, stomach cancers and esophageal cancers, breast cancers and prostatic cancers, which are regarded to produce a large number of CTCs.

In one embodiment, the present invention provides a cancer cell enrichment filter consisting of a substrate which has a plurality of through holes and at least a part of which is coated with the agent for improving cancer cell adhesiveness. This filter is capable of enriching cancer cells such as CTCs present in blood. Examples of the opening shape of each through hole include a circular shape, an elliptic shape, a rectangular shape, a rounded rectangular shape and a polygonal shape. A rounded rectangular shape is a shape having two long sides in the same length and two semicircles. From the viewpoint that cancer cells can be efficiently captured, a circular shape, a rectangular shape or a rounded rectangular shape is preferably employed. Besides, from the viewpoint of preventing clogging of the filter, a rounded rectangular shape is particularly preferably employed.

FIG. 1 is a schematic diagram illustrating one embodiment of the cancer cell enrichment filter. The filter 100 consists of a substrate 20 having a plurality of through holes 10. The opening shape of each through hole 10 is a rounded rectangular shape. CTCs are captured on a surface of a face 30 of the substrate 20. At least a part of the face 30 is coated with the agent for improving cancer cell adhesiveness. The agent for improving cancer cell adhesiveness is preferably coated over the whole of the face 30. A part or the whole of a face opposite to the face 30 may be coated with the agent for improving cancer cell adhesiveness.

As a method for applying the agent for improving cancer cell adhesiveness to the surface of the substrate of the cancer cell enrichment filter or the like, a coating method is the most generally employed. The coating method is performed by allowing a solution of the polymer comprising the constitutional unit represented by the above formula (1) to adhere to the substrate surface by a dipping method, a spraying method, a spin coating method or the like, and then removing (drying) the solvent. A thickness of a film attained after drying the solvent is preferably 0.01 µm to 1.0 mm, more preferably 0.1 to 100 µm and further more preferably 0.5 to 50 µm. If the film thickness is smaller than 0.01 µm, non-adhesiveness to blood cell components and adhesiveness to cancer cells may not be sufficiently exhibited in some cases. Alternatively, if the film thickness exceeds 1.0 mm, it is apprehended that balance between these adhesiveness characteristics may be lost in some cases.

In order to more strongly fix the agent for improving cancer cell adhesiveness on the substrate, the substrate may be heated after coating with the agent for improving cancer cell adhesiveness. Furthermore, the polymer comprising the constitutional unit represented by the above formula (1) may be crosslinked. An example of a crosslinking method includes precedent addition of a crosslinkable monomer to the materials of the polymer. For the crosslinkage, electron beams, y rays or light irradiation may be used.

For forming, on the substrate surface, a layer of the polymer comprising the constitutional unit represented by the above formula (1) by plasma graft polymerization, plasma-initiated polymerization is performed with the monomer represented by the above formula (2) supplied after irradiation of low-temperature plasma performed under reduced pressure of approximately $1.3 \times 10^{-1}$ Pa, preferably 1.3 to 133.3 Pa, and under an atmosphere of argon, nitrogen, air, any of various monomers or the like for 1 to 300 seconds, preferably 2 to 30 seconds.

In one embodiment, the material and the shape of the substrate are not especially limited, and for example, a porous body, fiber, nonwoven fabric, a film, a sheet or a tube may be employed. Examples of the material of the substrate include natural polymers such as cotton and hemp; synthetic polymers such as nylon, polyester, polyacrylonitrile, polyolefin, halogenated polyolefin, polyurethane, polyamide, polysulfone, polyether sulfone, poly(meth)acrylate, a halogenated polyolefin ethylene-polyvinyl alcohol copolymer and a butadiene-acrylonitrile copolymer; and mixtures thereof. Examples of the material also include metals, ceramics and composite materials thereof, and the substrate may include a plurality of substrates.

Examples of the metal include but are not limited to noble metals such as gold and silver; base metals such as copper, aluminum, tungsten, nickel and chromium; and alloys of these metals. Such a metal may be singly used, or may be used as an alloy with another metal or as a metal oxide for imparting functionality. From the viewpoint of the price and availability, nickel, copper or a metal containing any of them as a principal component is preferably used. Here, a principal component means a component occupying 50% by weight or more among materials contained in the substrate. Such a metal may be subjected to photolithography or the like for forming through holes therein, so as to be used as a screen filter.

A general CTC has a diameter of 10 µm or more. Here, a diameter of a cell means a length of the longest straight line out of straight lines each connecting arbitrary two points on the outline of the cell in observation with a microscope. From the viewpoint of the permeability of blood and CTC capturing performance, the through holes of the cancer cell enrichment filter have an average pore size of preferably 5 µm or more and less than 30 µm and an average aperture ratio of preferably 5% or more and less than 50%. Furthermore, the average pore size and the average aperture ratio are respectively more preferably 5 µm or more and less than 15 µm and 10% or more and less than 40% and particularly preferably 5 µm or more and less than 10 µm and 20% or more and less than 40%. Here, an aperture ratio means an area occupied by the through holes in the whole area of the filter. From the viewpoint of preventing clogging, the average aperture ratio is preferably larger, but if it exceeds the upper limit, the filter may be degraded in its strength or may be difficult to be worked in some cases. Alternatively, if the aperture ratio is lower than 5%, the cancer cell enrichment performance of the filter may be degraded in some cases.

Herein, a pore size in an opening shape other than a circular shape, such as an elliptic shape, a rectangular shape or a rounded rectangular shape, is defined as the maximum value of diameters of spheres that can pass through the through hole in such a shape. If the opening shape is a rectangular shape, the pore size of the through hole corresponds to the length of the short side of the rectangle, and if the opening shape is a polygonal shape, it corresponds to the diameter of the inscribed circle of the polygon. If the opening shape is a rectangular shape or a rounded rectangular shape, even when CTCs and leucocytes are captured by the through holes, there remains a space in the long side direction of the opening shape. Since a liquid can pass through this space, the clogging of the filter can be prevented.

The thickness of the substrate of the filter is preferably 3 to 100 μm, more preferably 5 to 50 μm and particularly preferably 10 to 30 μm. If the thickness of the substrate is smaller than 3 μm, the filter may be degraded in its strength and hence may be difficult to handle in some cases. Alternatively, if the thickness of the substrate exceeds 100 μm, the materials may be consumed in an amount more than necessary or it may take longer time to work the substrate, and hence, such a large thickness may be disadvantageous in cost and precise working of the substrate itself may become difficult in some cases.

Subsequently, a method for producing the cancer cell enrichment filter of this embodiment will be described. The method for producing the filter of this embodiment is not especially limited, and the filter is produced by, for example, an electrocasting method (an electroforming method). The electrocasting method is a method in which a thick electroplating is provided on a matrix and is then peeled off. First, a photosensitive resist film (a photosensitive layer) is adhered onto a support of stainless steel or the like. Next, a mask having a pattern of the opening shape of the through holes of the filter is fixed on the photosensitive layer. Subsequently, light (activating light beams) is irradiated through the mask. After the light irradiation, if the support remains on the photosensitive layer, the support is removed, and then, development is carried out by removing an unexposed portion by wet development with a developer such as an alkaline aqueous solution, a water-based developer or an organic solvent, or by dry development or the like, and thus, a resist pattern is formed. Thereafter, the developed resist pattern is used as a mask, so as to plate portions not masked but exposed on the substrate. Examples of a plating method include copper plating, solder plating, nickel plating and gold plating. After the plating, the resulting plating layer is peeled off from the support and the photosensitive layer, and thus, the plating layer is obtained. When at least a part of the plating layer is coated with the agent for improving cancer cell adhesiveness by the aforementioned method, the cancer cell enrichment filter is obtained.

In one embodiment, the present invention provides a method for detecting presence of cancer cells comprising a filtration step of filtering a sample with the cancer cell enrichment filter. As a sample for enriching cancer cells such as CTCs, blood pooled in a bone marrow, a spleen, a liver or the like, lymph, a tissue fluid, cord blood or the like may be used, but peripheral blood circulating through a body can be most easily used. It is useful means for determining the progression of a cancer to detect the presence of CTCs in peripheral blood.

The method for detecting presence of cancer cells of this embodiment can be practiced by, for example, incorporating the cancer cell enrichment filter in a flow channel, introducing peripheral blood into the flow channel for enriching cells including CTCs, and determining whether or not there are CTCs in the enriched cells. Blood is introduced into the flow channel by, for example, a method in which a pressure is applied from an inlet direction of the flow channel, a method in which a pressure is reduced from an outlet direction of the flow channel, or a method in which a peristaltic pump is used. Furthermore, the area of the used filter is suitably 1 to 10 cm$^2$ if, for example, CTCs are enriched from 1 mL of blood.

When CTCs are enriched by the aforementioned method, not only the CTCs but also blood cells such as leucocytes are simultaneously enriched. Therefore, it is necessary to determine whether or not cancer cells are contained in collected cells. For example, after enriching the CTCs by the aforementioned method, cells can be verified as cancer cells by dyeing them with an antibody against a fluorescent labeled cancer marker. An example of the antibody against a cancer marker includes an anti-EpCAM antibody.

Alternatively, cells can be verified as cancer cells by analyzing a gene of the cells having been enriched by the aforementioned method. For example, the cells can be verified as cancer cells by analyzing mutation of a gene such as p53, K-RAS, H-RAS, N-RAS, BRAF or APC. Besides, the gene analysis result can be used for, for example, determining a subsequent treatment course of a patient. Alternatively, the cells can be verified as cancer cells by measuring telomerase activity or the like of the cells having been enriched by the aforementioned method.

Since the filtration step merely slightly damages the cells, the enriched cells can be cultured for performing more detailed analysis.

EXAMPLES

The present invention will now be described based on examples. It is noted that the present invention is not limited to the following examples.

Experiment Example I-1

Synthesis of Polymethoxyethyl Acrylate

Polymethoxyethyl acrylate having a constitutional unit of the above formula (1) in which $R^1$ is hydrogen, $R^2$ is a methyl group and m is 1 was synthesized. Specifically, 15 g of methoxyethyl acrylate was polymerized in 60 g of 1,4-dioxane at 75° C. for 10 hours with nitrogen bubbling by using azobisisobutyronitrile (0.1% by mass) as an initiator. After the polymerization was completed, the resultant was added dropwise to n-hexane to form a precipitate, and thus the product was isolated. The product was dissolved in tetrahydrofuran, the resulting solution was purified with n-hexane twice, and the resultant was dried under reduced pressure for a whole day and night. Thus, a clear and colorless polymer with high viscosity was obtained. The yield rate was 76%. As a result of analysis of the thus obtained polymer by gel permeation chromatography (GPC), the polymer was found to have a number average molecular weight of 15,000 and a molecular weight distribution (Mw/Mn) of 3.4.

The molecular weight of the polymer was calculated in terms of standard polystyrene molecular weight under the following GPC measurement conditions:
Pump: PU Intelligent HPLC Pump (manufactured by Jasco Corporation)
Column: GPC K804 (manufactured by Showa Denko K.K., Shodex)
Eluent: chloroform
Measurement temperature: room temperature
Flow rate: 1.0 mL/min
Detector: Jasco RI-1530 RI (manufactured by Jasco Corporation)

Experiment Example I-2

Preparation of Nickel Substrate

A commercially available titanium plate was immersed, as a cathode, in an electrolytic bath for electrolytic nickel plating (that is, an aqueous solution of 450 g/L of nickel sulfamate, 5 g/L of nickel chloride and 30 g/L of boric acid, 55° C.), and an anode was immersed in the same electrolytic bath. With a voltage applied to the both electrodes, nickel plating was performed to attain a film thickness of 10 μm, and thus, a nickel substrate was prepared.

Experiment Example I-3

Coating and Verification of Nickel Substrate

Figure 2:
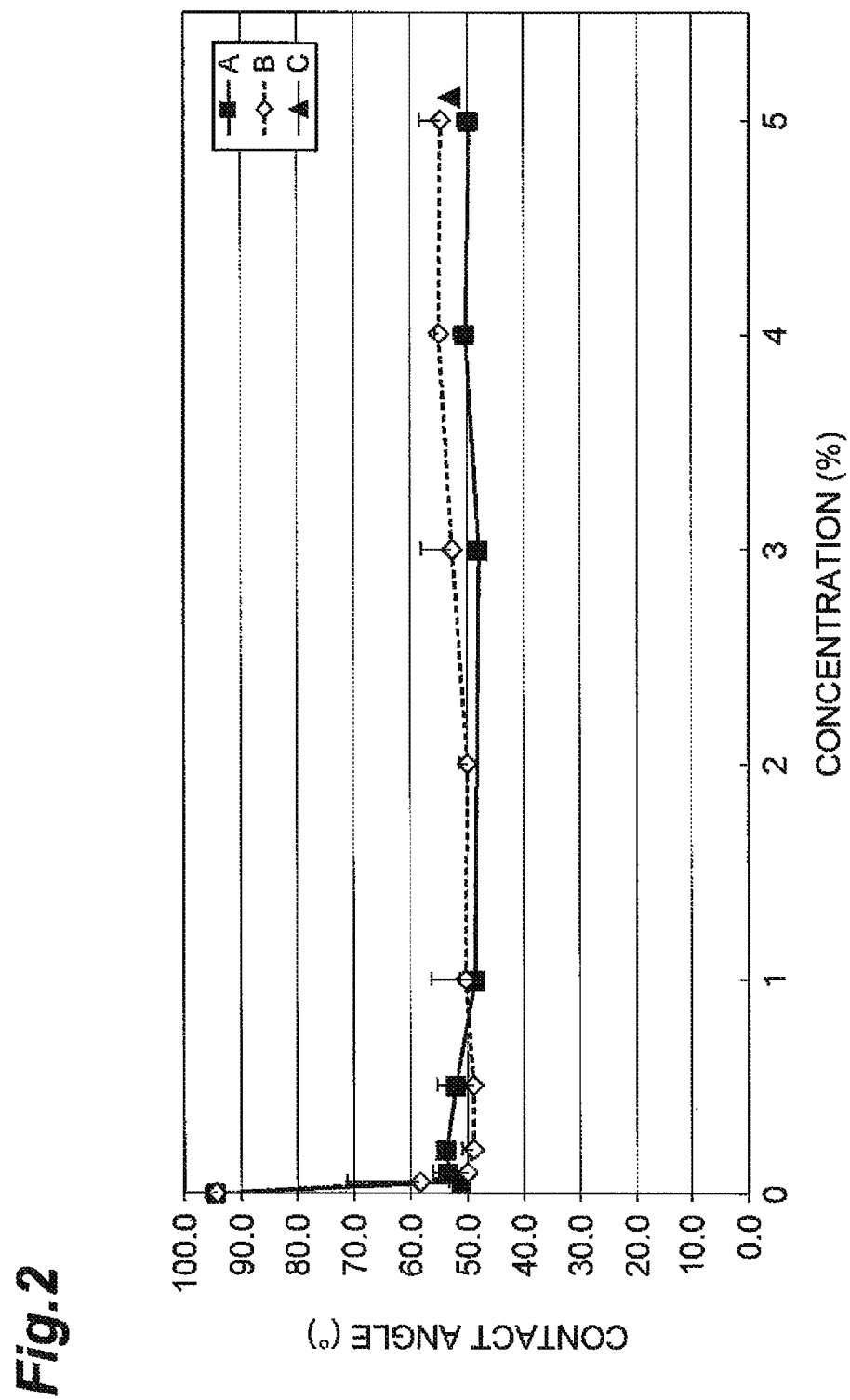
FIG. 2 is a graph showing results of Experiment Example I-3, in which A corresponds to a result obtained in applying a polymer solution once, B corresponds to a result obtained in applying the polymer solution twice and C corresponds to a result obtained by a positive control.

The polymer synthesized in Experiment Example I-1 was dissolved in chloroform, so as to obtain a plurality of polymer solutions different in the concentration in a range from 0 to 5% by mass. Each of the polymer solutions was applied (casted) onto the nickel substrate prepared in Experiment Example I-2 and the solvent was dried, so as to coat the surface of the nickel substrate. Two types of substrates, that is, one coated with the polymer once and the other coated with the polymer twice, were prepared. As a positive control, a polyethylene terephthalate substrate to which 40 μL of polymer solution was applied was used. A contact angle of water was measured on each of these substrates, so as to verify that the substrate was coated with the polymer. For measuring a contact angle, a contact angle measuring apparatus (Erma Inc., Model G-1-100) was used. A static contact angle was measured 30 seconds after dropping 2 μl of pure water onto the surface of each substrate. FIG. 2 is a graph showing the results obtained in Experiment Example I-3. The abscissa indicates the concentration of the polymer and the ordinate indicates the contact angle of water. In FIG. 2, A corresponds to the result obtained in applying the polymer solution once, B corresponds to the result obtained in applying the polymer solution twice, and C corresponds to the result of the positive control.

Experiment Example I-4

Preparation of Substrate

The polymer synthesized in Experiment Example I-1 was dissolved in chloroform for obtaining a solution in a concentration of 4% by mass. This solution was applied onto the nickel substrate prepared in Experiment Example I-2 and the solvent was dried, so as to coat the surface of the nickel substrate with the polymer, and thus, a nickel substrate of Example I-1 was prepared. The polymer solution was applied twice. Through X-ray photoelectron spectroscopy (Shimadzu Corporation, ESCA-1000), a peak of nickel derived from the nickel substrate was not observed but peaks of carbon and oxygen derived from the polymer were detected, and thus, it was verified that the nickel substrate was coated with the polymer. Furthermore, the nickel substrate prepared in Experiment Example I-2 was used as a nickel substrate of Comparative Example I-1.

Test for Cancer Cell Adhesiveness

Onto each of the nickel substrates of Example I-1 and Comparative Example I-1, 1.0 mL of cancer cell suspension adjusted to 10,000 cells/mL in a medium containing 10% of blood serum was dropped with a pipette, and the resulting substrates were allowed to stand still at 37° C. for 60 minutes. As the cancer cells, human fibrosarcoma cell line HT-1080 was used. Subsequently, the substrates were rinsed with a physiological buffered saline solution, and the number of cells adhered onto each substrate was counted. In order that the cells could be easily counted, the cells were fixed with formaldehyde, and then, cell nuclei were dyed with 4,6-diamino-2-phenylindole (DAPI). The number of cell nuclei was counted by using a confocal laser scanning microscope (Olympus Corporation, FV-1000), and the thus obtained number was defined as the number of cells.

Figure 3:
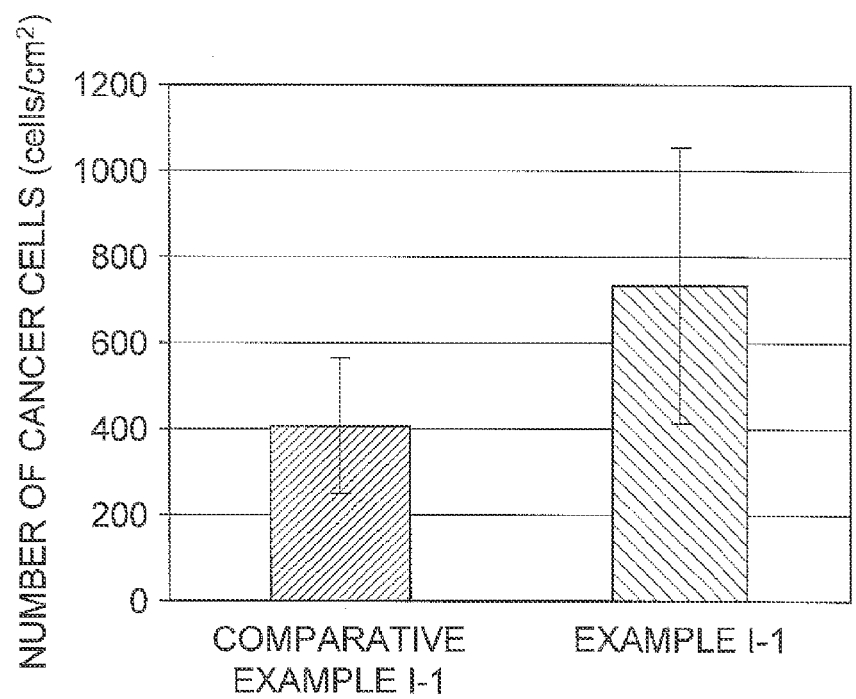
FIG. 3 is a graph showing results of Experiment Example I-4.

FIG. 3 is a graph showing the results of Experiment Example I-4. The experiment was carried out five times on each substrate, and the results are shown as a mean±standard deviation. In the nickel substrate of Example I-1, the number of adhered cancer cells was larger than in the nickel substrate of Comparative Example I-1. With respect to a large number of other cancer cells, similar results were verified.

Experiment Example I-5

Preparation of Substrate

In the same manner as in Experiment Example I-4, the nickel substrates of Example I-1 and Comparative Example I-1 were used for an experiment.

Test for Blood Platelet Adhesiveness

Onto each of the nickel substrates of Example I-1 and Comparative Example I-1, 0.2 mL of fresh human platelet-rich plasma anticoagulated with sodium citrate was dropped with a pipette, and the resulting substrates were allowed to stand still at 37° C. for 60 minutes. Subsequently, each substrate was rinsed with a phosphate buffer solution, and after fixation with glutaraldehyde, the substrate was observed with a scanning electron microscope, so as to count the number of blood platelets adhered in an area of $1 \times 10^4$ $\mu m^2$.

Figure 4:
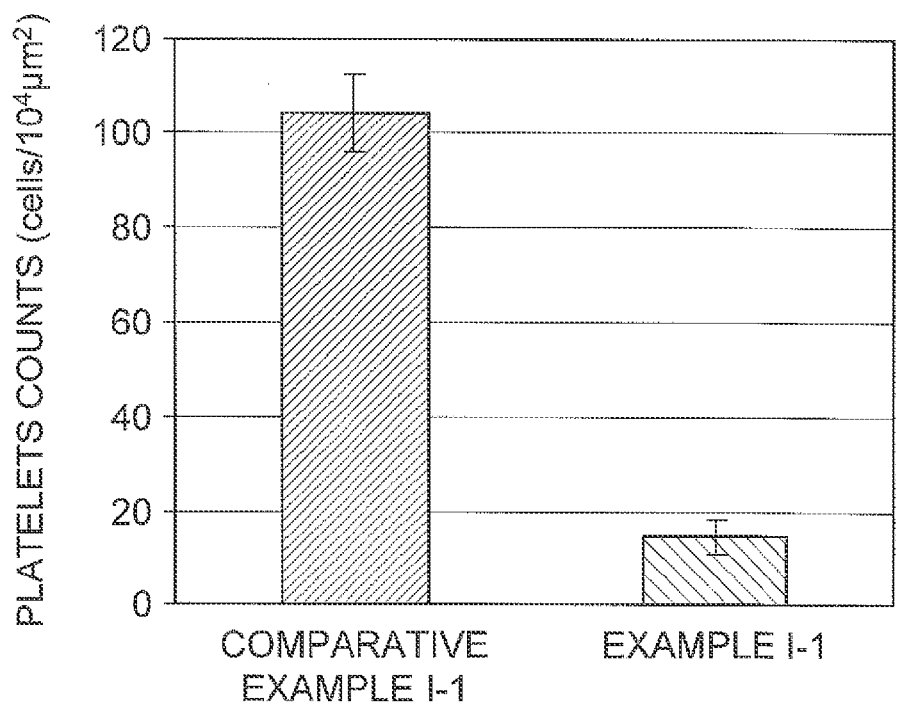
FIG. 4 is a graph showing results of Experiment Example I-5.

FIG. 4 is a graph showing the results obtained in Experiment Example I-5. The experiment was carried out five times on each substrate, and the results are shown as a mean±standard deviation. In the nickel substrate of Example I-1, the number of adhered blood platelets was smaller than in the nickel substrate of Comparative Example I-1.

It was revealed, based on the results of Experiment Examples I-4 and I-5, that the nickel substrate of Example I-1 shows improved adhesiveness to cancer cells but shows low adhesiveness to a blood cell component. Accordingly, when the agent for improving cancer cell adhesiveness of the present invention is applied to the surface of a cancer cell enrichment filter, the adhesiveness of cancer cells to the filter can be improved so as to improve the enrichment ratio of cancer cells.

Experiment Example II-1

Synthesis of poly[2-(2-ethoxyethoxy)ethyl acrylate]

Poly[2-(2-ethoxyethoxy)ethyl acrylate] having a constitutional unit represented by the above formula (1) in which $R^1$ is hydrogen, $R^2$ is an ethyl group and m is 2 was synthesized. Specifically, 15 g of 2-(2-ethoxyethoxy)ethyl acrylate was polymerized in 60 g of 1,4-dioxane at 75° C. for 10 hours with nitrogen bubbling by using azobisisobutyronitrile (0.1% by mass) as an initiator. After the polymerization was completed, the resultant was added dropwise to n-hexane to form a precipitate, and thus the product was isolated. The product was dissolved in tetrahydrofuran, and the resulting solution was purified with n-hexane twice. The resulting purified product was dried under reduced pressure for a whole day and night. Thus, a clear and colorless syrup-like polymer was obtained. The yield amount (the yield rate) was 11.4 g (76.0%). The structure of the thus obtained polymer was verified by 1H-NMR. As a result of analysis for the molecular weight by the GPC, the polymer was found to have a number average molecular weight (Mn) of 12,000 and a molecular weight distribution (Mw/Mn) of 3.9. The molecular weight of the polymer was calculated in terms of standard polystyrene molecular weight under the same GPC measurement conditions as in Experiment Example I-1.

Synthesis of poly[2-(2-methoxyethoxy)ethyl methacrylate]

Poly[2-(2-methoxyethoxy)ethyl methacrylate] having a constitutional unit represented by the above formula (1) in which $R^1$ is a methyl group, $R^2$ is a methyl group and m is 2 was synthesized. Specifically, 10 g of 2-(2-methoxyethoxy) ethyl methacrylate was polymerized in 50 g of 1,4-dioxane at 80° C. for 8 hours with nitrogen bubbling by using azobisisobutyronitrile (0.1% by mass) as an initiator. After the polymerization was completed, the resultant was added dropwise to n-hexane to form a precipitate, and thus the product was isolated. The product was dissolved in tetrahydrofuran, and the resulting solution was purified with n-hexane twice. The resulting purified product was dried under reduced pressure for a whole day and night. Thus, a clear and colorless syrup-like polymer was obtained. The yield amount (the yield rate) was 8.2 g (82.0%). The structure of the thus obtained polymer was verified by 1H-NMR. As a result of analysis for the molecular weight by the GPC, the polymer was found to have a number average molecular weight (Mn) of 104,000 and a molecular weight distribution (Mw/Mn) of 4.6. The molecular weight of the polymer was calculated in terms of standard polystyrene molecular weight under the same GPC measurement conditions as in Experiment Example I-1.

Synthesis of poly(2-methacryloyloxyethyl phosphorylcholine-co-butyl methacrylate)

Poly(2-methacryloyloxyethyl phosphorylcholine-co-butyl methacrylate) represented by the following formula (3) was synthesized. The poly(2-methacryloyloxyethyl phosphorylcholine-co-butyl methacrylate) is a copolymer of 2-methacryloyloxyethyl phosphorylcholine (MPC) and butyl methacrylate (BMA), and a ratio of MPC:BMA was 40:60 mol % to 1:99 mol %.

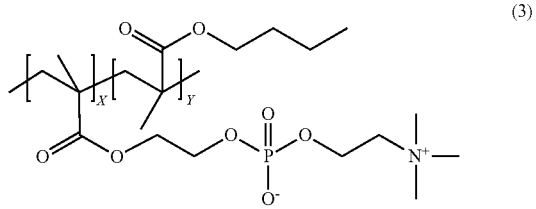

(3)

In the above formula (3), X and Y are 1 to 10,000, and X:Y is 40:60 mol % to 1:99 mol %.

Specifically, the monomers were dissolved in ethanol, and the polymerization was performed at 75° C. for 10 hours with nitrogen bubbling by using azobisisobutyronitrile (0.1% by mass) as an initiator. After the polymerization was completed, the resultant was added dropwise to diethyl ether to form a precipitate, and thus the product was isolated. The product was dissolved in ethanol, the resulting solution was purified with diethyl ether twice, and the resultant was dried under reduced pressure for a whole day and night. Thus, a white powder polymer was obtained. The yield rate was 51%. As a result of the analysis of the thus obtained polymer by the gel permeation chromatography (GPC), the polymer was found to have a number average molecular weight of 240,000 and a molecular weight distribution (Mw/Mn) of 2.9. The molecular weight of the polymer was calculated in terms of standard poly(oxyethylene) molecular weight under the same GPC measurement conditions as in Experiment Example I-1 except that ethanol/chloroform (2/8) was used as the eluent.

Experiment Example II-2

Preparation of Nickel Substrate

A nickel substrate was prepared in the same manner as in Experiment Example I-2.

Experiment Example II-3

The nickel substrate was coated with each of the polymers in the same manner as in (Experiment Example I-3), and a static contact angle of water was measured. As a result, in using the poly[2-(2-ethoxyethoxy)ethyl acrylate] in a concentration of 0.2% wt/vol or more, the contact angle was substantially stabilized at 25°. In using the poly[2-(2-methoxyethoxy)ethyl methacrylate] in a concentration of 0.5% wt/vol or more, the contact angle was substantially stabilized at 38°. In using the poly(2-methacryloyloxyethyl phosphorylcholine-co-butyl methacrylate) in a concentration of 0.1% wt/vol or more, the contact angle was substantially stabilized at 104°.

Experiment Example II-4

Preparation of Substrate

The four polymers synthesized in Experiment Examples I-1 and II-1 were respectively dissolved in chloroform for obtaining solutions each in a concentration of 4% by mass. Each of these solutions was applied to the nickel substrate prepared in Experiment Example II-2 and the solvent was dried, so as to coat the surface of the nickel substrate with the polymer, and thus, nickel substrates of Example II-1 (using polymethoxyethyl acrylate), Example II-2 (using poly[2-(2-ethoxyethoxy)ethyl acrylate]), Example II-3 (using poly[2-(2-methoxyethoxy)ethyl methacrylate] and Comparative Example II-1 (using poly(2-methacryloyloxyethyl phosphorylcholine-co-butyl methacrylate)) were prepared. Each polymer solution was applied twice. Through X-ray photoelectron spectroscopy (Shimadzu Corporation, ESCA-1000), a peak of nickel derived from the nickel substrate was not observed but peaks of carbon and oxygen derived from the polymer were detected, and thus, it was verified that each nickel substrate was coated with the corresponding polymer.

Test for Cancer Cell Adhesiveness

Onto each of the nickel substrates of Examples II-1 to II-3 and Comparative Example II-1, 1.0 mL of cancer cell suspension adjusted to 10,000 cells/mL in a medium containing 10% of blood serum was dropped with a pipette, and the resulting substrates were allowed to stand still at 37° C. for 60 minutes. As the cancer cells, human mammary adenocarcinoma cell line MDA-MB-231 was used. Subsequently, the substrates were rinsed with a physiological buffered saline solution, and the number of cells adhered onto each substrate was counted.

In order that the cells could be easily counted, the cells were fixed with formaldehyde, and then, cell nuclei were dyed with 4,6-diamino-2-phenylindole (DAPI). The number of cell nuclei was counted by using a confocal laser scanning microscope (Olympus Corporation, FV-1000), and the thus obtained number was defined as the number of cells.

Figure 5:
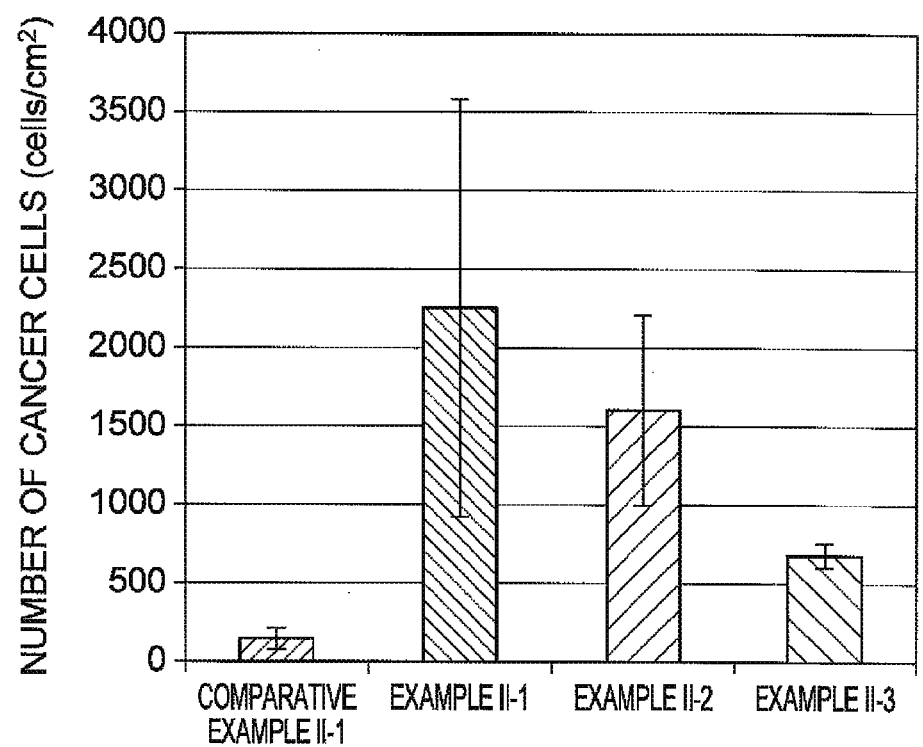
FIG. 5 is a graph showing results of Experiment Example II-4.

FIG. 5 is a graph showing the results of Experiment Example II-4. The experiment was carried out five times on each substrate, and the results are shown as a mean±standard deviation. The nickel substrate of Example II-1 captured 2000 or more cancer cells. The nickel substrate of Example II-2 captured 1500 or more cancer cells. The nickel substrate of Example II-3 captured 500 or more cancer cells. On the contrary, the nickel substrate of Comparative Example II-1 captured merely approximately 140 cancer cells.

Experiment Example III-1

Synthesis of poly[2-(2-ethoxyethoxy)ethyl methacrylate]

Poly[2-(2-ethoxyethoxy)ethyl methacrylate] having a constitutional unit represented by the above formula (1) in which $R^1$ is a methyl group, $R^2$ is an ethyl group and m is 2 was synthesized. Specifically, 15.0 g ($7.4 \times 10^{-2}$ mol) of 2-(2-ethoxyethoxy)ethyl methacrylate was dissolved in 58.2 mL of 1,4-dioxane to be subjected to $N_2$ purge for 2 hours. To the resultant, 15.1 mg ($9.2 \times 10^{-2}$ mmol) of azobisisobutyronitrile used as an initiator dissolved in a small amount of 1,4-dioxane was added, and the polymerization was performed under a nitrogen atmosphere at 75° C. for 2 hours and 10 minutes. Purification was performed by using hexane. The reaction solution was added dropwise to 1500 mL of hexane serving as a poor solvent, and the solvent was removed by decantation. To the thus obtained crude polymer, approximately 50 mL of tetrahydrofuran (THF) was added for dissolving, and the resulting solution was added dropwise to 1000 mL of hexane again for forming a precipitate, and then the solvent was removed by the decantation. This operation was repeated once again, so that the monomer and the initiator contained in the polymer could be completely removed. The resultant was dried under reduced pressure overnight, and the mass of the resulting polymer was measured. Thus, a clear and colorless syrup-like polymer, poly[2-(2-ethoxyethoxy)ethyl methacrylate], was obtained. The yield amount was 5.36 g and the yield rate was 35.7%. As a result of analysis for the molecular weight by the GPC, the polymer was found to have a number average molecular weight (Mn) of 142,000 and a molecular weight distribution (Mw/Mn) of 6.06. The molecular weight of the polymer was calculated in terms of standard polystyrene molecular weight under the same GPC measurement conditions as in Experiment Example I-1.

Experiment Example III-2

Preparation of Nickel Substrate

A nickel substrate was prepared in the same manner as in Experiment Example I-2.

Experiment Example III-3

With the nickel substrate coated with the polymer in the same manner as in Experiment (Example I-3), a static contact angle of water was measured, resulting in finding that the contact angle was substantially stabilized at 78° in using the poly[2-(2-ethoxyethoxy)ethyl methacrylate] in a concentration of 0.5% wt/vol or more.

Experiment Example III-4

Preparation of Substrate

The five polymers synthesized in Experiment Examples I-1, II-1 and III-1 were respectively dissolved in chloroform for obtaining solutions each in a concentration of 4% by mass. Each of these solutions was applied to the nickel substrate prepared in Experiment Example III-2 and the solvent was dried, so as to coat the surface of the nickel substrate with the polymer, and thus, nickel substrates of Example III-1 (using polymethoxyethyl acrylate), Example III-2 (using poly[2-(2-ethoxyethoxy)ethyl acrylate]), Example III-3 (using poly[2-(2-methoxyethoxy)ethyl methacrylate], Comparative Example III-1 (using poly(2=methacryloyloxyethyl phosphorylcholine-co-butyl methacrylate)) and Example III-4 (using poly[2-(2-ethoxyethoxy)ethyl methacrylate]) were prepared. Each polymer solution was applied twice. Through the X-ray photoelectron spectroscopy (Shimadzu Corporation, ESCA-1000), a peak of nickel derived from the nickel substrate was not observed but peaks of carbon and oxygen derived from the polymer were detected, and thus, it was verified that each nickel substrate was coated with the corresponding polymer.

Test for Cancer Cell Adhesiveness

Onto each of the nickel substrates of Examples III-1 to III-4 and Comparative Example III-1, 1.0 mL of cancer cell suspension adjusted to 10,000 cells/mL in a medium containing 10% of blood serum was dropped with a pipette, and the resulting substrates were allowed to stand still at 37° C. for 60 minutes. As the cancer cells, lung cancer cell line A549 was used. Subsequently, the substrates were rinsed with a physiological buffered saline solution, and the number of cells adhered onto each substrate was counted. In order that the cells could be easily counted, the cells were fixed with formaldehyde, and then, cell nuclei were dyed with 4,6-diamino-2-phenylindole (DAPI). The number of cell nuclei was counted by using a confocal laser scanning microscope (Olympus Corporation, FV-1000), and the thus obtained number was defined as the number of cells.

Figure 6:
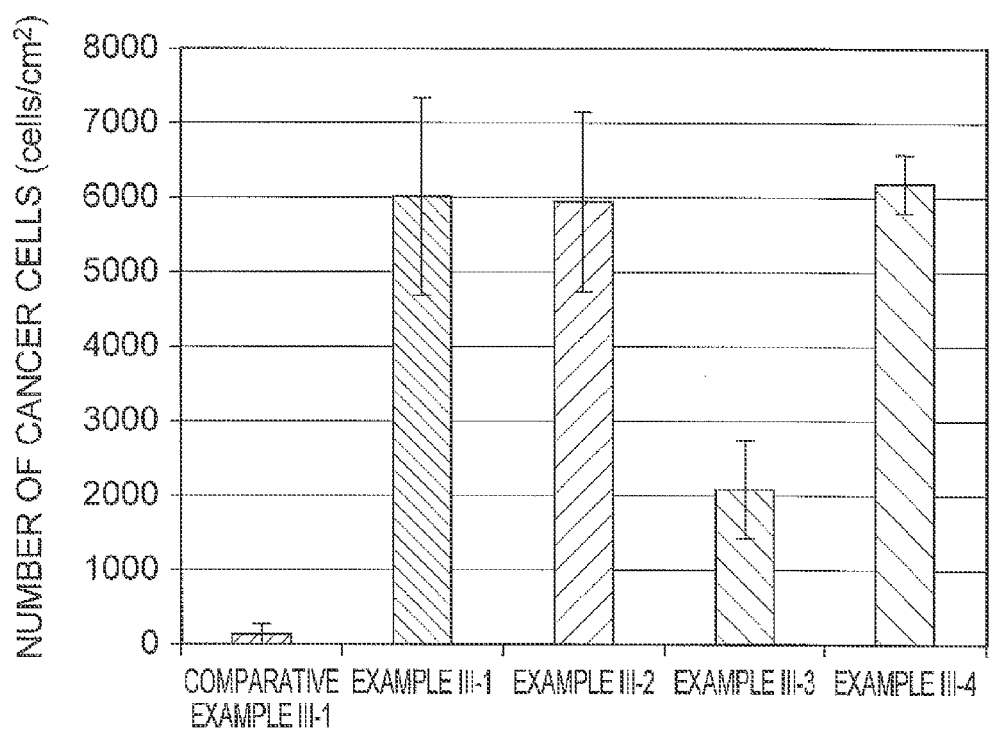
FIG. 6 is a graph showing results of Experiment Example III-4.

FIG. 6 is a graph showing the results of Experiment Example III-4. The experiment was carried out five times on each substrate, and the results are shown as a mean±standard deviation. The nickel substrates of Example III-1 and III-4 captured 6000 or more cancer cells per $cm^2$. The nickel substrate of Example III-2 captured 5000 or more cancer cells per $cm^2$. The nickel substrate of Example III-3 captured 2000 or more cancer cells per $cm^2$. On the contrary, the nickel substrate of Comparative Example III-1 captured merely approximately 130 cancer cells per $cm^2$.

REFERENCE SIGNS LIST

10 . . . through hole, 20 . . . substrate, 30 . . . face, 100 . . . filter.

The invention claimed is:
1. A cancer cell enrichment filter comprising:
 a substrate having a plurality of through holes, wherein at least a part of the substrate is coated with an agent for improving cancer cell adhesiveness, the agent for improving cancer cell adhesiveness consisting of a polymer comprising a constitutional unit represented by the following formula (1);

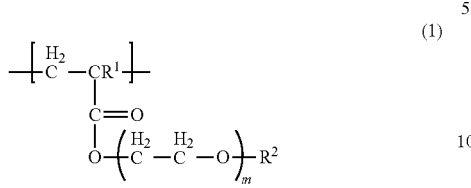

wherein (i) $R^1$ is a hydrogen atom, $R^2$ is an ethyl group, and m is 2 or (ii) $R^1$ is a methyl group, $R^2$ is a methyl group and m is 2.

2. The cancer cell enrichment filter according to claim 1, wherein the polymer consists of the constitutional unit represented by the formula (1).

3. The cancer cell enrichment filter according to claim 1, wherein $R^1$ is a hydrogen atom, $R^2$ is an ethyl group and m is 2.

4. The cancer cell enrichment filter according to claim 1, wherein $R^1$ is a methyl group, $R^2$ is a methyl group and m is 2.

5. The cancer cell enrichment filter according to claim 1, wherein a number average molecular weight of the polymer is 10,000 to 300,000.

6. The cancer cell enrichment filter according to claim 1, wherein the through holes have an average pore size of 5 μm or more and less than 30 μm and an average aperture ratio of 5% or more and less than 50%.

7. The cancer cell enrichment filter according to claim 1, wherein the substrate is made of a metal.

8. The cancer cell enrichment filter according to claim 7, wherein the metal is selected from the group consisting of copper, nickel, a copper-nickel alloy, and copper, nickel or copper-nickel alloy having a gold-plated surface.

9. A method for detecting presence of cancer cells, comprising:
a filtration step of filtering peripheral blood with the cancer cell enrichment filter according to claim 1.

10. The method according to claim 9, further comprising:
a step of analyzing a gene of cells having been enriched in the filtration step.

11. The method according to claim 9, further comprising:
a step of culturing cells having been enriched in the filtration step.

12. A method for improving adhesiveness of cancer cells to a substrate comprising a step of coating the substrate with a polymer comprising a constitutional unit represented by the following formula (1):

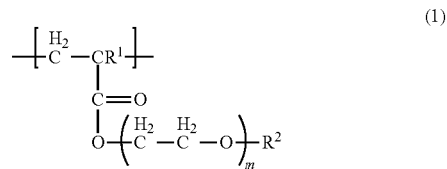

wherein (i) $R^1$ is a hydrogen atom, $R^2$ is an ethyl group, and m is 2 or (ii) $R^1$ is a methyl group, $R^2$ is a methyl group and m is 2.

13. The method according to claim 12, wherein the polymer consists of the constitutional unit represented by the formula (1).

14. The method according to claim 12, wherein $R^1$ is a hydrogen atom, $R^2$ is an ethyl group and m is 2.

15. The method according to claim 12, wherein $R^1$ is a methyl group, $R^2$ is a methyl group and m is 2.

16. The method according to claim 12, wherein a number average molecular weight of the polymer is 10,000 to 300,000.

* * * * *